United States Patent [19]

Anderson et al.

[11] Patent Number: 5,647,857
[45] Date of Patent: Jul. 15, 1997

[54] PROTECTIVE INTRALUMINAL SHEATH

[75] Inventors: Scott C. Anderson, Sunnyvale; James M. Cannon, Jr., Santa Clara, both of Calif.

[73] Assignee: Endotex Interventional Systems, Inc., Menlo Park, Calif.

[21] Appl. No.: 405,511

[22] Filed: Mar. 16, 1995

[51] Int. Cl.$^6$ .......................... A61M 5/00; A61M 25/00
[52] U.S. Cl. .......................... 604/264; 604/160; 604/161
[58] Field of Search .................. 604/264, 280, 604/96, 160, 161, 286, 14, 15, 171; 606/108, 192, 194; 215/254; 229/238, 239, 309–314, 316, 926; 623/1

[56] References Cited

U.S. PATENT DOCUMENTS

| | | | |
|---|---|---|---|
| 4,345,606 | 8/1982 | Littleford | 607/122 |
| 4,581,025 | 4/1986 | Timmermans . | |
| 4,665,918 | 5/1987 | Garza et al. . | |
| 4,732,152 | 3/1988 | Wallstén et al. . | |
| 4,733,665 | 3/1988 | Palmaz . | |
| 4,787,899 | 11/1988 | Lazarus . | |
| 4,830,003 | 5/1989 | Wolff et al. . | |
| 4,848,343 | 7/1989 | Wallstén et al. . | |
| 4,893,623 | 1/1990 | Rosenbluth . | |
| 4,922,905 | 5/1990 | Strecker . | |
| 4,969,890 | 11/1990 | Sugita et al. . | |
| 5,071,407 | 12/1991 | Termin et al. . | |
| 5,137,512 | 8/1992 | Burns et al. . | |
| 5,158,548 | 10/1992 | Lau et al. . | |
| 5,167,634 | 12/1992 | Corrigan, Jr. et al. | 604/160 |
| 5,192,297 | 3/1993 | Hull . | |
| 5,195,978 | 3/1993 | Schiffer | 604/161 |
| 5,242,399 | 9/1993 | Lau et al. | 604/104 |
| 5,246,452 | 9/1993 | Sinnott . | |
| 5,250,033 | 10/1993 | Evans et al. | 604/160 |
| 5,306,294 | 4/1994 | Winston et al. . | |
| 5,324,269 | 6/1994 | Miraki | 604/160 |
| 5,360,401 | 11/1994 | Turnland . | |
| 5,366,472 | 11/1994 | Hillstead . | |
| 5,496,345 | 3/1996 | Kieturakis et al. | 606/192 |

*Primary Examiner*—Michael Powell Buiz
*Assistant Examiner*—V. Alexander
*Attorney, Agent, or Firm*—Fish & Neave; Nicola A. Pisano

[57] ABSTRACT

A sheath holds a device against a balloon catheter for delivery in the lumen of a patient. The device can be a stent and graft combination. The stent is kept properly centered over the balloon catheter by the sheath as the graft is placed in a blood vessel. The smooth outer surface of the sheath protects the vessel wall from the rough surface of the stent. A notch is formed in the end of the sheath where the free end of a strand of thread protrudes from the sheath. The sheath is removed from the graft by pulling on the free end of the strand otherwise located distally from the outer surface of the sheath. The strand cuts through and splits open the sheath as a result of the force applied on the free end of the strand. The other end of the strand is attached to a reinforced collar at the other end of the sheath. The strand does not cut through the collar. After reaching the collar, the proximal force applied on the strand now pulls the split sheath from the graft and stent combination without disturbing the placement of the stent over the balloon delivery catheter.

20 Claims, 2 Drawing Sheets

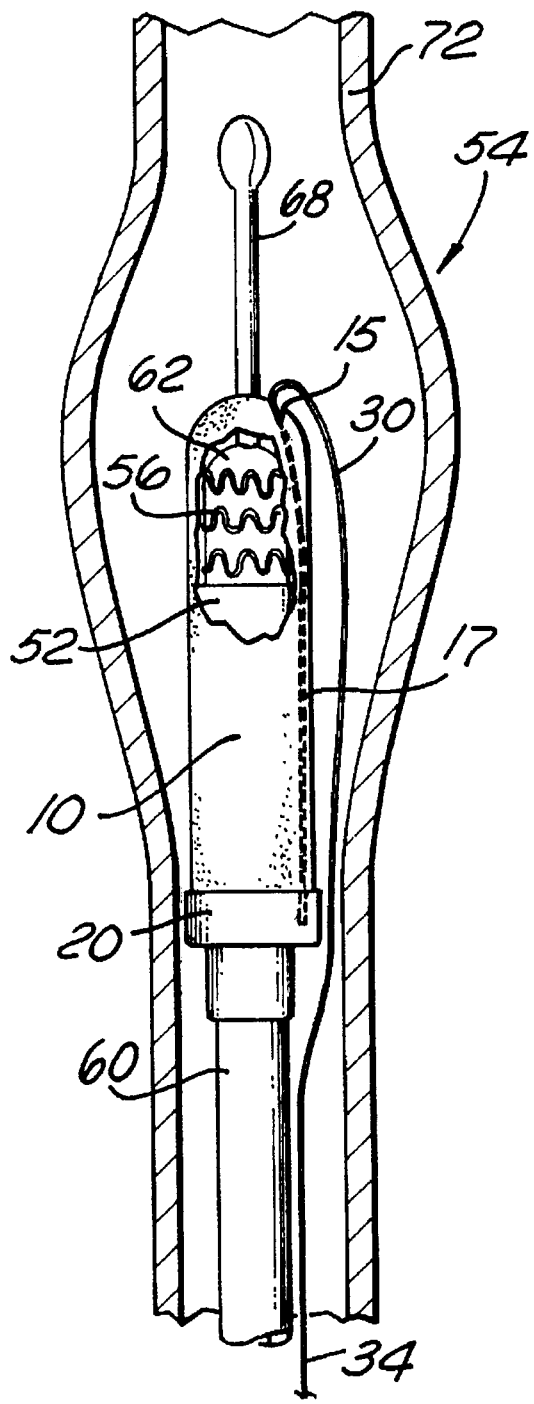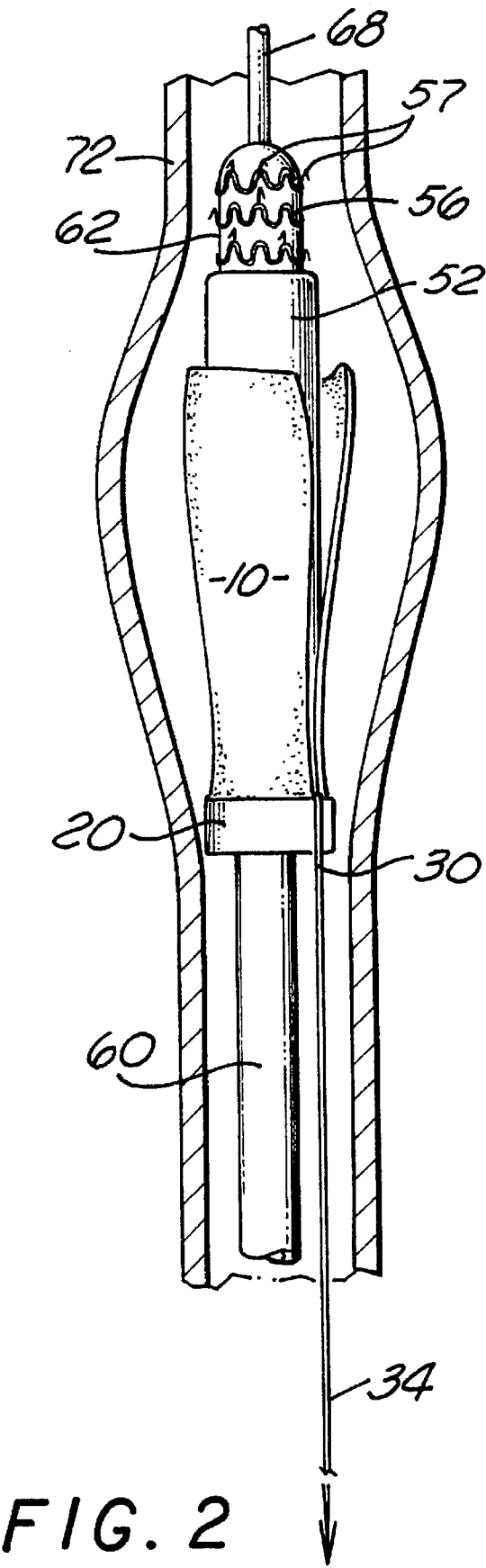
FIG. 1
FIG. 2

PROTECTIVE INTRALUMINAL SHEATH

BACKGROUND OF THE INVENTION

The invention relates generally to endoprostheses and, more specifically, to a sheath for protecting an intraluminal prosthesis and the patient when delivering and deploying the prosthesis to an area of a body lumen that has been weakened by damage or disease. The sheath of the present invention is also envisioned to be used with such prostheses as a graft for treating aneurysms of the abdominal aorta, or an intraluminal stent for repairing coronary arteries.

An abdominal aortic aneurysm (AAA) is an abnormal dilation of the arterial wall of the aorta in the region of the aorta that passes through the abdominal cavity. The condition most commonly results from atherosclerotic disease. Frequently, abdominal aortic aneurysms are dissecting aneurysms, that is aneurysms that are formed when there is a tear or fissure in the arterial lining or wall through which blood is forced and eventually clots, forming a thrombosis which swells and weakens the vessel. Abdominal aortic aneurysms do not cause pain, but are easily detected in a thorough physical examination. If the aneurysm is not detected and treated, it is likely to rupture and cause massive hemorrhaging fatal to the patient.

Treatment of AAAs comprises some form of arterial reconstructive surgery which commonly is referred to as a "triple-A" procedure. One such method is by-pass surgery, in which an incision is made into the abdominal cavity, the aorta is closed off above and below the site of the aneurysm, the aneurysm is resected, and a synthetic graft or tube sized to approximate the diameter of the normal aorta is sutured to the vessel to replace the aneurysm and to allow blood flow through the aorta to be reestablished. The graft commonly is fabricated of a biocompatible material that is compliant and thin-walled. Nylons and synthetic fibers have been found to be suitable for the construction of the graft. The mortality rate associated with this surgical procedure is favorable (less than 5%) when it is performed prior to rupture of an aneurysm. However, patients having an AAA typically are over 65 years of age, and often have other chronic illnesses which increase the risk of perioperative or post-operative complications. Those patients thus are not ideal candidates for this type of major surgery. Further, it has been pointed out that this procedure is not often successfully resorted to after an aneurysm has ruptured (the mortality rate increases to over 65%) because of the extensiveness of the surgery and the time required to prepare a patient for it.

Because of the aforementioned disadvantages to conventional surgical methods, another procedure was developed as an alternative to conventional, major surgery. This method also involves emplacement of a graft at the site of the aneurysm. The graft is deployed there by being routed through the vascular system carried by a catheter, wire or other device suitable for negotiating the vasculature. The graft and its deployment system often are introduced into the blood stream percutaneously with a femoral approach and the entire procedure can be performed using local rather than general anesthesia.

Once the graft has been positioned at the aneurysm, it is disengaged from the delivery system and can be affixed to the aortic wall both distally and proximally of the aneurysm. The graft is positioned in the vessel spanning the site of the aneurysm such that the walls of the graft are generally parallel to the walls of the affected area of the aorta. The aneurysm thus is excluded from the circulatory system by the graft rather than being resected altogether. If the aneurysm is a dissecting type and a thrombosis exists between the walls of the aorta, the now-excluded aneurysm may beneficially provide structural support for the graft.

Grafting systems often include an attachment system for deploying the graft. A tubular system, often referred to as a stent, may be fitted coaxially within the graft, and which can extend out of the graft at either or both the proximal and distal ends thereof. The attachment system often has a lattice or open weave structure, which can provide flexibility and promote rapid endothelial tissue growth through the structure once the graft has been deployed. The attachment system may include hook-like elements for penetrating the intimal walls to attach the graft to the aorta, or those hook-like elements may be provided on the graft itself.

The actual function of delivering the graft may be accomplished by inflating the balloon of a catheter by introducing pressurized fluid into a lumen of the catheter from a source external to the patient. Inflation of the balloon applies a force to the graft and any attachment system supplied therein which extends radially and presses the graft and attachment system into the vessel wall above and below the aneurysm. To avoid premature detachment of the graft and to prevent the attachment elements from damaging the vessels or halting the forward movement of the system while the graft is being routed to the treatment site, a protective capsule or sheath is often provided to protect and contain the graft until such time as deployment is desired.

The sheath helps hold the graft and stents onto the catheter and prevents direct contact of the elements of the combination with the walls of the vessel while the system is being advanced to the treatment site, thus protecting the vascular system of the patient from hazardous protrusions such as sharp edges on the stents. A rod or wire may be connected to the sheath and may extend proximally along the length of the catheter so that it can be manipulated by the physician exterior to the patient and retracted (proximally) at the time of deployment. Alternatively, the sheath can traverse the entire length of the catheter, and can be retracted (proximally) from outside the patient to expose the graft-and-stent combination. However, in either instance, the manipulative elements of the sheath may be relatively bulky and awkward to use, and may interfere with the precise placement of the graft and with the operation of the graft delivery system.

As used herein, reference to the "proximal" is toward the outside of the patient and away from the stent and graft while reference to the "distal" is toward the stent and graft on the balloon portion of the catheter. The proximal and distal references apply to directions in the vascular system such as the aorta.

It should be noted that sheaths are often used with other implantable devices, including intraluminal stents for delivery to the coronary artery. Percutaneous transluminal coronary angioplasty (PTCA) is a widely practiced procedure for treating coronary artery disease. In a typical PTCA procedure, a dilation catheter having an inflatable balloon is advanced through a patient's arterial system until the balloon crosses an atherosclerotic lesion. The balloon is inflated at a relatively high pressure so as to compress the atherosclerotic plaque of the lesion against the inside of the artery wall and dilate the artery. The balloon is then deflated to a small profile for removal from the patient's vasculature, and blood flow resumes through the dilated artery. To help prevent abrupt closure, dissection, or restenosis, a physician can implant an intravascular prosthesis or stent to maintain vascular patency inside the artery at the lesion. The stent may be delivered to the lesion site by a balloon catheter which then expands the stent to a larger diameter. The stent is left in the artery, either temporarily or permanently, at the side of the dilated lesion.

The stent may have protuberances on its outer surface facing the patient's lumen wall. Should such protuberances rub against the lumen wall during delivery of the stent, they may damage the lumen wall and cause the stent to be displaced from the catheter. The sheath holds the stent onto the catheter and prevents the stent from damaging the lumen walls while the stent is being delivered to the treatment site, thus protecting the vascular system of the patient from any sharp edges on the stents. However, as noted above, the manipulative elements of the sheath can be relatively bulky and awkward to use, and may interfere with the precise placement of the stent and with the operation of the catheter/stent delivery system.

In order for a stent to be used advantageously with the endoprosthesis systems described above for the treatment and repair of body lumen, an improved sheath is desirable for preventing the stent surface (possibly including hooks on the stent) from abrading the vessel wall. The improved sheath should keep the stent properly centered over the balloon catheter delivery system as the graft is deployed in the vessel. It would also be useful to remove the sheath from the graft without disturbing the precise placement of the stent over the balloon so that the graft may be properly implanted in the vessel. Although various sheaths have been proposed, none adequately provides all of these desirable features.

What is needed in the art of such implantable devices is a sheath which holds the stent tightly against a balloon delivery catheter, wherein the catheter can be removed without disturbing the precise placement of the stent over the balloon. The sheath should also be capable of being used with a variety of implantable devices, including various catheter/stent/graft combinations, for delivery anywhere in the body. The present invention satisfies this need.

SUMMARY OF THE INVENTION

The present invention is directed to a sheath for use with catheter delivery systems for repairing diseased or injured vessels and may be used for treating aneurysms. The present invention may be employed with a stent-and-graft combination for treating aneurysms, or an intraluminal stent for treating coronary artery diseases. In any event, the present invention should not be construed as being limited to those specific applications. The sheath of the present invention can be used with various catheter-stent-graft combinations for delivery anywhere in the body, including the aorta and the coronary arteries. The sheath tightly packs the stent against the catheter shaft so a low profile can be maintained while the combination is being routed to the treatment site. The sheath of the present invention and the system for its removal is novel and unique.

The stent-and-graft stent and graft combination can be readily delivered to the aneurysm by mounting the combination on a balloon portion of a delivery catheter, and passing the assembly through the vasculature to the implantation site. A variety of means for securing the stent-and-graft stent and graft combination to the catheter during delivery is available. Presently, it is preferred to compress the stent onto the balloon and retain the stent on the balloon using a protective sheath.

In a preferred embodiment of the invention, the sheath includes a sheath body having an outer surface, a first sheath end and a second sheath end; a collar located at the second sheath end; and a strand having a first strand end located distally from the outer surface of the sheath from the collar to the first sheath end, and a free strand end extending from the first sheath end. Applying a proximal force on the free strand end causes the first strand end to cut through the sheath from the first end to the collar, wherein the collar is resistant to being cut by the first strand end.

One feature of the invention is to prevent the rough stent surface from abrading the vessel wall.

Another feature of the invention is to keep the stent properly centered over the balloon catheter delivery system as the graft is deployed in the vessel.

Yet another feature of the invention is to remove the sheath from the graft without disturbing the precise placement of the stent over the balloon so that the graft may be properly implanted in the vessel.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, of a preferred embodiment of the sheath according to the invention incorporated into a graft delivery system.

FIG. 2 is an elevational view of the embodiment of the sheath shown in FIG. 1 after being split according to the invention.

DETAILED DESCRIPTION OF THE PREFERRED EMBODIMENTS

Figure 3:
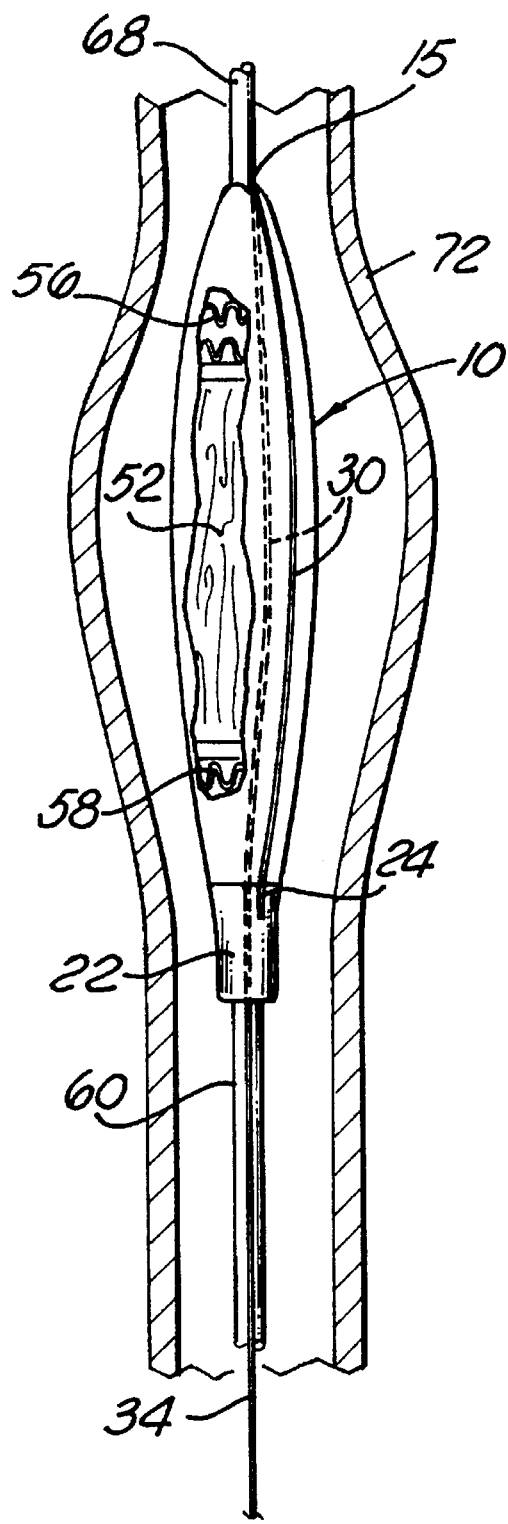
FIG. 3 is an elevational view, partially in section, of another preferred embodiment of the sheath according to the invention.

The invention relates to a sheath which is used in conjunction with atraumatically inserted devices for repairing body lumens of all types. As described herein, reference is made to a stent-and-graft combination for repairing an aortic aneurysm. Reference will also be made to a intraluminal stent for repairing coronary arteries in conjunction with the present invention. However, other devices may be equally suited to receive the sheath of the present invention.

One preferred method of incorporating sheath 10 of the present invention into a graft delivery system is illustrated in FIG. 1. The graft delivery system includes a multilumen catheter 60 of the type used in other percutaneous procedures for deploying stents, grafts or other prostheses to repair portions of blood vessels. The operative end of catheter 60 includes a balloon for installing prostheses such as a stent-and-graft combination. Sheath 10 holds the stent-and-graft combination tightly onto the catheter, and assists in providing a small cross profile for the combination. The stent is kept properly centered over the delivery catheter as the combination is pushed into place in the vessel. Sheath 10 has a smooth outer surface for protecting the vascular walls from the rough surfaces of stents and other prostheses. Sheath 10 is shown in FIG. 1 to cover the stent-and-graft, and may further extend to cover part of the catheter itself. The sheath may extend to cover substantially the entire length of the catheter. Sheath 10 may be any suitable length to maintain the stent in place over the catheter. Removal of the sheath from the above catheter-stent-graft by unzition may be effected by unzipping or splitting open the body of the sheath as will be discussed in more detail.

Sheath 10 includes a notch 15 formed on one end and a collar 20 located on the opposite end of sheath 10. Collar 20 acts as a reinforcement at an end of sheath 10, and may be formed from a doubled-over portion of the sheath body. Strand 30 is a strong thin flexible biocompatible thread or fiber filament that is connected to collar 20. Strand 30 is located away from the outer sheath surface, and travels from collar 20 to the notch 15 on the opposite end of sheath 10. Strand 30 may be embedded within the body of sheath 10, or placed underneath, between sheath 10 and the stent-and-graft combination. Strand 30 further includes a free end 34 extending away from sheath 10 at notch 15. The free end 34 of the strand doubles back past collar 20 towards the proximal end of the catheter.

The body of sheath 10 is preferably composed of a PET ("polyethyleneterapthalate") heatshrink material. PET is a preferable material because it is strong, thin, biocompatible, and tears easily after being notched. A suitable wall thickness for sheath 10 may be 0.005 inches or 0.0125 centimeters. However, those skilled in the art will recognize that other thicknesses are also suitable, depending upon the application and specific use of sheath 10. Furthermore, the use of heatshrink techniques allows a device, such as stent-and-graft combination, to be packed tightly against a catheter shaft to reduce the cross profile of the device to be intraluminally inserted.

Delivery catheter 60 is used to deploy tubular graft 52 at the site of abdominal aortic aneurysm 54 via stent 56. The catheter has a first lumen extending along its length which is in communication with an expandable member or balloon disposed at the distal end of the catheter. Pressurized fluid or gas can be introduced into the balloon lumen to inflate the balloon, and to exert an outward radial force on anything disposed about the balloon.

The catheter has a second lumen through which guidewire 68 passes. The guidewire is advanced through the vasculature of a patient beyond the site of aneurysm as a preliminary step in the graft delivery procedure. After the guidewire 68 has been positioned, the catheter 60 carrying the sheathed stent-and-graft combination is advanced over the guidewire.

After stent 56 has been attached to graft 52, the stent-and-graft combination is loaded onto the distal end of catheter 60. The combination is positioned so that stent 56 overlies balloon 62 and the graft rests over and is substantially coaxial with the catheter. It is important that the graft and stent remain in this position until the deployment function is accomplished.

Sheath 10 can be removed without disturbing the precise placement of the stent 56 over the balloon by using the strand 30 to split open sheath 10 for facilitating its simple removal. Although FIGS. 1 and 2 show the sheath covering only the stent-and-graft combination, it should be noted that the invention is not so limited. Sheath 10 may extend beyond the stent-and-graft combination and further encompass the shaft of catheter 60. Sheath 10 is removed after being unzipped or split open. The free end 34 of strand 30 exits away from sheath 10 and extends proximally along the length of the catheter to where the free strand end 34 can be manipulated by a physician exterior to the patient. As shown in FIG. 2, by applying a proximal force to pull the strand 30 away from the sheath 10, strand 30 cuts and splits the length of sheath 10 apart from the notch 15 to the collar 20. Collar 20 is resistent to the cutting force of strand 30. Collar 20 may be formed of any suitable material which is sufficiently resistant to the cutting force of strand 30 so as to act as a stop. As noted earlier, collar 20 may be a doubled-over segment of sheath material, or a separate plastic element. Notch 15 encourages the propagation of the split along sheath 10.

As noted earlier, strand 30 may be built into or embedded in an extrusion of the body of sheath 10. Such construction may take the form of a thickened path for the strand 30 along the wall of the sheath 10. A flaw 17 may be built into the sheath to encourage the propagation of a split. The flaw 17 is preferably a perforation formed in the body of sheath 10. Strand 30 may be configured in any suitable manner along the body of sheath 10 to create a desired split therealong. A plurality of strands may be used to create multiple splits in the sheath.

After sheath 10 is unzipped or split, stent 56 is no longer compressed against catheter 60, and sheath 10 can be pulled off from the stent and graft combination with relative ease. Continued traction on strand 30 tugs on collar 20 to remove the split sheath 10 from over the combination without disturbing the precise placement of the stent over the balloon catheter in the vessel.

The sheath is withdrawn (proximally) to expose the stent-and-graft combination, and the catheter is advanced so that the stent-and-graft combination span the aneurysm. The entire sheath 10 can be pulled out of the patient without disturbing the placement of the stent-and-graft combination. The balloon 62 is inflated by the pressurized fluid or gas source external to the patient, and the radial forces accompanying expansion of the balloons are applied to expand both the graft and the stents radially outward, pressing both elements against aortic wall 72 proximal to and distal to the aneurysm. Attachment elements or hooks 57 are provided on stent 56 for attaching the stent and graft combination to the intima or aortic wall.

As shown in FIG. 3, instead of covering only a portion of the combination, sheath 10 may alternately be extended to entirely cover both the stent and the graft. Such an extended configuration would be advantageous for covering a combination where two stents 56 and 58 are used at opposite ends of the graft 52. Collar 20 may include a tough biocompatible coaxial tube 22 surrounding the catheter shaft. Coaxial tube 22 surrounds a portion of the catheter shaft, and may extend to cover substantially the entire length of the catheter shaft. A cleft 24 may be found along a substantial length of coaxial tube 22 to form a split therealong in order to ease the removal of sheath 10 from along the shaft and operative end of catheter 60. Such a split in coaxial tube 22 would be advantageous should coaxial tube 22 cover a substantial length of catheter 60. Cleft 24 may be a fault similar to flaw 17 to be cut through by strand 30, or a preformed split in coaxial tube 22. In any event, cleft 24 does not span the entire length of coaxial tube 22.

The free end 34 of strand 30 may be situated to travel within the circumference of coaxial tube 22 and alongside of the catheter. In such an arrangement, part of the strand could be located outside the sheath, or embedded near the outer surface of the sheath, so as to cut into the sheath bodyas proximal force is applied to the free end 34 of strand 30.

Figure 4:
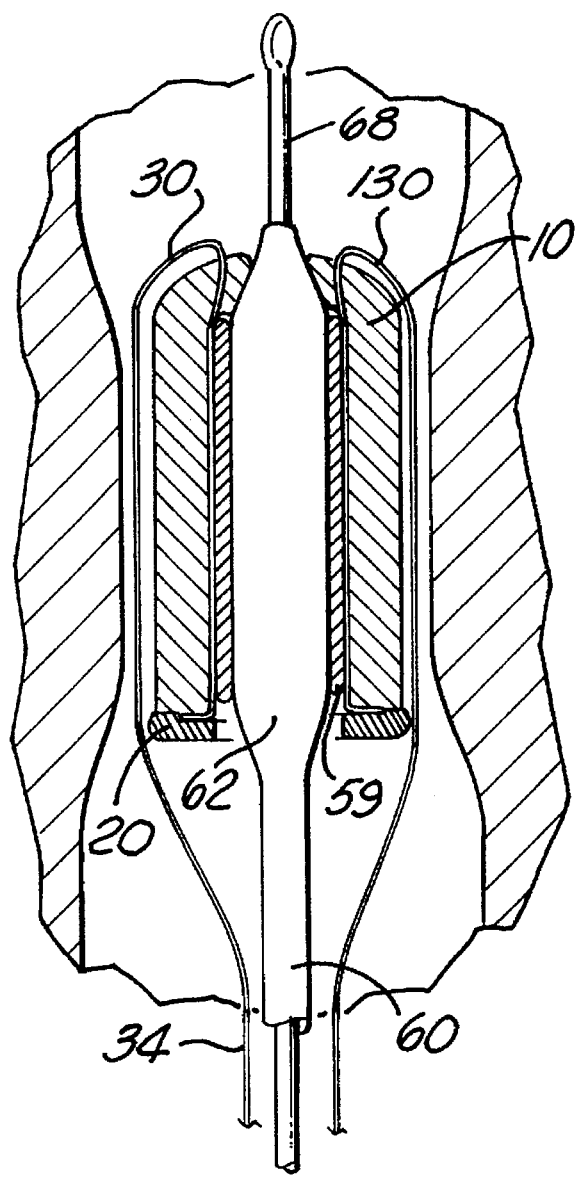
FIG. 4 is a sectional view of another preferred embodiment of the sheath according to the invention incorporated with a coronary stent delivery system disposed within an arterial region.

FIG. 4 shows another embodiment of the invention used in combination with an intraluminal coronary stent 59 for treating coronary artery disease. As discussed above, PTCA treatment does not require the use of a graft. Sheath 10 is similar to that shown in the prior embodiments. Strand 30 is shown travelling underneath sheath 10, between the body of sheath 10 and the outer surface of coronary stent 59. As noted earlier, the strand may also be embedded in an extrusion of the body of the sheath. A plurality of strands may be used to split the sheath for removal. For example, a second strand 130 is shown in FIG. 4, which complements strand 30. Applying a proximal force on both strands 30 and 130 creates multiple splits in sheath 10. Once stent 59 is properly positioned in the blood vessel, sheath 10 is removed and withdrawn proximally to expose stent 59 in the same manner as described for the graft-and-stent combination of FIGS. 1–3.

While the invention has been illustrated and described in terms of its use as a protective device for the delivery of a graft to treat an aneurysm, or a coronary stent to treat coronary artery disease, it will be apparent to those skilled in the art that the sheath can be used in other instances in other vessels of the body. The sheath of the present invention has the novel features of splitting the sheath by pulling on the remote free end of an otherwise embedded strand of thread so as to remove the sheath prior to implantation of the graft without disturbing the placement of the stent-and-graft configuration. This feature, coupled with the fact that the sheath tightly holds the stent-and-graft combination against the balloon delivery catheter, provides highly desirable protection for various types of prostheses for endoluminal treatment. Other modifications and improvements, such as varying the route of the strand within the sheath to split the sheath at two or more points or to keep the strand better contained within the sheath, may be made without departing from the scope of the invention.

I claim:

1. A retractable sheath for use with a catheter for delivering treatment to a body lumen of a patient, said sheath comprising:
   a tubular sheath body for covering a treatment-delivering portion of the catheter and having an inner surface, an outer surface, a proximal end and a distal end;
   a collar radially disposed about and attached to said proximal end of said sheath body;
   a strand including a peelable portion having a first end and a free portion having a free end; said peelable portion being embedded in said inner surface of said sheath body and extending axially from said collar to said distal end of said sheath body, said first end of said peelable portion being affixed to said collar and said free portion of said strand extending out of said distal end of said sheath body and resting alongside said outer surface of said sheath body further extending back towards said proximal end of said sheath body;
   whereby the proximal application of a tearing force to said free end of said free portion of said strand causes said peelable portion to cut through said sheath body up to said collar, said collar being resistant to the tearing force applied.

2. A sheath according to claim 1, wherein said distal end of said sheath body includes a notch, to facilitate the tearing of said sheath body by said peelable portion of said strand upon proximal application of a tearing force.

3. A sheath according to claim 1, wherein said sheath body further includes a perforation extending axially from said distal end towards said proximal end, to encourage the propagation of said peelable portion of said strand through said sheath body upon proximal application of a tearing force.

4. A sheath according to claim 1, wherein said collar is formed from a first layer and a second layer of said proximal end of said sheath body, said first layer doubled over said second layer of said proximal end of said sheath body so that said collar is resistant to the tearing force of said strand.

5. A sheath according to claim 1, wherein said collar further comprises a coaxial tube.

6. A sheath according to claim 5, wherein said coaxial tube is provided with a cleft to form a split along said tube for facilitating the removal of said sheath from the catheter.

7. A displaceable sheath intended for use with a catheter for delivering treatment to a body lumen of a patient, said sheath comprising:
   a hollow sheath body for covering a treatment-delivering portion of the catheter, said sheath body having an inner surface, an outer surface, an open proximal end, and a distal end having an aperture;
   a collar radially disposed about and affixed to said open proximal end of said sheath body; and
   a first strand including a first peelable portion with a first collar end and a first free portion adjacent said first peelable portion having a first free end, said first collar end of said first peelable portion being affixed to said collar and said first peelable portion extending from said collar along said inner surface of said sheath body and out of said aperture in said distal end of said sheath body, and said first free portion of said first strand extending back from said distal end of said sheath body back towards said open proximal end of said sheath body against said outer surface of said sheath body;
   whereby the proximal application of a tearing force to said first free end of said first free portion of said first strand causes said first peelable portion to cut through said sheath body up to said collar, said collar being resistant to the tearing force applied.

8. A sheath according to claim 7, wherein said aperture in said distal end of said sheath body includes a notch, to facilitate the tearing of said sheath body by said first peelable portion of said first strand upon proximal application of a tearing force.

9. A sheath according to claim 7, wherein said sheath body further includes a perforation extending axially from said distal end towards said proximal end, to encourage the propagation of said first peelable portion of said first strand through said sheath body upon proximal application of a tearing force.

10. A sheath according to claim 7, wherein said collar is formed from a first layer and a second layer of said proximal end of said sheath body, said first layer doubled over said second layer of said proximal end of said sheath body so that said collar is resistant to the tearing force of said first strand.

11. A sheath according to claim 7, wherein said collar further comprises a coaxial tube.

12. A sheath according to claim 11, wherein said coaxial tube is provided with a cleft to form a split along said tube for facilitating the removal of said sheath from the catheter.

13. A sheath according to claim 7, further comprising a second strand including a second peelable portion with a second collar end and a second free portion adjacent said second peelable portion having a second free end, said second collar end of said second peelable portion being affixed to said collar and said second peelable portion extending from said collar along said inner surface of said sheath body and out of said aperture in said distal end of said sheath body, and said second free portion of said second strand extending back from said distal end of said sheath body back towards said open proximal end of said sheath body against said outer surface of said sheath body;
   whereby the proximal application of a tearing force to said second free end of said second free portion of said second strand causes said second peelable portion to cut through said sheath body up to said collar, said collar being resistant to the tearing force applied.

14. A method of protecting a vessel wall from damage during the implantation of a medical device in a patient with a delivery catheter whereby the medical device is surrounded by a protective sheath, the sheath comprising a sheath body having an inner surface, an outer surface, a proximal end and a distal end, a collar affixed to said proximal end, a strand affixed to said collar, routed along the inner surface of the sheath body and having a free portion that extends out of the distal end of the sheath body and having a free end, said method comprising the steps of:

loading the medical device to be implanted on the delivery catheter;

surrounding the medical device with the sheath;

orienting the free portion of the strand so that it lies alongside the outer surface of the sheath body and extends towards the proximal end of the sheath body;

inserting the delivery catheter in the body lumen of a patient while preventing the free end from entering the lumen;

routing the catheter so that the device carried thereon and which is protected by the sheath is positioned at the site at which implantation is to occur;

pulling the free end of the strand proximally of the patient to cause the strand to slice through the sheath body up to the collar;

pulling further on the free end of the strand to apply a force to the collar, which collar is resistant to being cut by the strand, to cause the collar to travel proximally along the catheter and thus pull the severed sheath away from the medical device so that implantation then can be accomplished.

15. The method of claim 14, wherein the proximal end of the sheath body includes a notch, and the step of orienting the free portion of the strand further includes the step of orienting the free portion of the strand so that it rests in the notch.

16. The method of claim 14, wherein the collar comprises a portion of the proximal end of the sheath body that is doubled back on itself.

17. The method of claim 14, wherein the portion of the strand that is routed along the inner surface of the sheath body is embedded in the sheath body.

18. The method of claim 14, wherein the collar is a coaxial tube surrounding the delivery catheter.

19. The method of claim 14, wherein the medical device to be implanted is an intraluminal stent.

20. The method of claim 14, wherein the medical device to be implanted is a stent-and-graft combination.

* * * * *